United States Patent
Kulkarni et al.

(10) Patent No.: US 6,727,365 B1
(45) Date of Patent: Apr. 27, 2004

(54) PROCESS FOR THE PREPARATION OF VINYLPYRIDINE FROM PICOLINE OVER MODIFIED ZEOLITES

(76) Inventors: Shivanand Janardan Kulkarni, Indian Institute of Chemical Technology, Hyderabad 500 007, Andhra Pradesh (IN); Gangapuram Madhavi, Indian Institute of Chemical Technology, Hyderabad, Andra Pradesh (IN); Venkataraman Viswanathan, Indian Institute of Chemical Technology, Hyderabad 500 007, Andhra Pradesh (IN); Kondapuram Vi jaya Raghavan, Indian Institute of Chemical Technology, Hyderabad 500 007, Andhra Pradesh (IN)

( * ) Notice: Subject to any disclaimer, the term of this patent is extended or adjusted under 35 U.S.C. 154(b) by 0 days.

(21) Appl. No.: 10/285,402

(22) Filed: Oct. 31, 2002

(51) Int. Cl.[7] ............................................. C07D 213/28
(52) U.S. Cl. ...................................................... 546/352
(58) Field of Search ......................................... 546/352

(56) References Cited

U.S. PATENT DOCUMENTS

2002/0123633 A1 * 9/2002 McAteer et al. ............ 546/352

* cited by examiner

*Primary Examiner*—Patricia L. Morris
(74) *Attorney, Agent, or Firm*—Maryellen Feehery; Nanda P. B. A. Kumar; Reed Smith LLP

(57) ABSTRACT

The present invention relates to an improved eco-friendly process for the preparation of vinylpyridine from corresponding picoline over modified zeolite catalyst in vapour phase which comprises reacting picoline with formaldehyde with a molar ratio of formaldehyde to picoline in the range of 1:1 to 4:1, at a temperature ranging between 200° C. to 450° C., at a weight hourly in the range of 0.25 $hr^{-1}$–1.00 $hr^{-1}$ over a modified commercial zeotlite catalyst to obtain a high yield and selectivity of the desired product.

13 Claims, No Drawings

PROCESS FOR THE PREPARATION OF VINYLPYRIDINE FROM PICOLINE OVER MODIFIED ZEOLITES

FIELD OF INVENTION

The present invention relates to an improved process for preparing vinylpyridine from corresponding picoline. The present invention relates to a process for the preparation of 2-vinylpyridine or 4-vinylpyridine over modified zeolite catalysts. In particular, it relates to method for the synthesis of vinylpyridine from corresponding picoline with formaldehyde in vapour phase in an eco-friendly method with high yield and selectivity.

This invention provides a non-corrosive, eco-friendly process, where the catalyst can be recycled and reused for many times. 2-vinylpyridine and 4-vinylpyridine are useful starting material in polymer industry.

BACKGROUND OF THE INVENTION 2-vinylpyridine (2-VP) is an important monomer used in synthesizing various polymers. Butadiene and styrene monomers were used with 2-vinylpyridine to form latex terpolymer that bonded fabric cords to the rubber matrix of tires. The addition product of methanol and 2-vinylpyridine, 2-(2-methoxy-ethyl) pyridine is a veterinary anthelmintic. This monomer is prepared commercially by autoclaving acetylene, acrylonitrite using cobaltocene catalyst or oxidative dehydrogenation of 2-ethylpyridine on Cr—Nb catalyst (Y. Wakatsuki, synthesis, 1, 26 (1976)). ("Heterocyclic compounds: Pyridine and Pyridine derivatives part 2, Ed. E. Klingsberg, Chapt. V, p 203). Generally in most of the processes, the synthesis of 2-vinylpyridine is practiced by a two-step procedure, which involves a base catalyzed addition of 2-picoline to formaldehyde to give 2-(2-hydroxy ethyl) pyridine followed by dehydration to 2-vinylpyridine monomer. (S. Yasuda, H. Niwa and O. Tagano, Jpn. Kokai Tokyo, Koho 78, 141281 (1978)). 2-vinylpyridine was prepared with 70.8% selectivity at 35.8% conversion over $ZrO_2$ catalyst (Reddy B. N. and Subrahrnanyam M, Catalysis Present & Future, Eds. Kanta Rao P. & Beniwal R. S. p. 304(1995)). The synthesis of vinylpyridines are also reported by the dehydrogenation of alkyl pyridines over $V_2O_5/MgO$ and $MoO_3/MgO$ catalysts in the presence of $O_2$. The alkylation of pyridine, 2,3, and 4-picolines with methanol as alkylating agent over alkali metal ion exchanged X and Y type zeolites in $N_2$ atmosphere resulted in the formation of side-chain alkylated products like ethylpyridines and vinylpyridines were 22.2, and 5.3% at 82.0% conversion over CsY catalyst from 2-picoline and methanol at 450° C. However considerable amounts of ring-alkylated derivatives (lutidines) were formed simultaneously. (Kshiwagi H., Enomoto S., Chem. Pharm. Bull., 30(2), 404(1982)).

The alkylation of picolines with methanol was studied over modified X and Y zeolites in which the major products were ethylpyridine and vinylpyridine (Chem. Pharm. Bull., 30(2), 404, 1982). The yields of ethylpyridine were more when the CsY zeolite was used at 450° C. On the other hand the yields of vinylpyridines were more over CsX zeolite at about 425° C. The yields of vinylpyridines were <20–25%. The syntheses of vinylpyridines were also reported by the dehydrogenation of alkylpyridines over $V_2O_5/MgO$ and $MoO_3/MgO$ catalysts in the presence of oxygen. However the yields and selectivities of 4-vinylpyridine were lower

OBJECTIVES OF THE INVENTION

The main objective of the present invention is to provide a process for the synthesis of vinylpyridines over modified zeolites in a heterogeneous eco-friendly method.

Another objective of the present invention is to provide a process for the preparation of 2-vinylpyridine in high yield and high selectivity.

Another object of the present invention is to provide a process for the preparation of 4-vinylpyridine in high yield and high selectivity.

Another object of the present invention is to provide a process for the preparation of 2-vinylpyridine from 2-picoline and formaldehyde in the presence of catalyst which comprises ZSM-5 containing one or two element(s) from alkali and/or alkaline earth metal ions, like $Na^+$, $K^+$, $Rb^+$, $Cs^+$, $Mg^{+2}$, $Ca^{+2}$, $Sr^{+2}$, etc., which can be recycled and reused for several times.

Still another object of the present invention is to provide a process for the preparation of 4-vinylpyridine from 4-picoline and formaldehyde in the presence of a catalyst which comprises ZSM-5 containing one or two element(s) from alkali and alkaline earth metal ions, like Na, K, Rb, Cs, Mg, Ca, Sr, Ba etc., which can be recycled and reused for several times.

SUMMARY OF THE INVENTION

Accordingly, the present invention provides a process for the preparation of 2-vinylpyridine from 2-picoline and formaldehyde in vapour phase over 2-picoline and formaldehyde in vapour phase over modified zeolite/molecular sieve. The catalyst comprises of particularly ZSM-5 modified with sodium, potassium, rubidium, cesium, magnesium, calcium, and/or barium, etc as cation or species.

The present invention also provides a process for the preparation of 4-vinylpyrdine from 4-picoline and formaldehyde in vapour phase over modified zeolite/molecular sieve. The catalyst comprises of ZSM-5 modified with sodium, potassium, rubidium, cesium, magnesium, calcium or barium.

DETAILED DESCRIPTION OF THE INVENTION

Accordingly, the present invention provides an improved process for the preparation of vinylpyridine from corresponding picoline over modified zeolite catalyst in vapour phase which comprises reacting picoline with formaldehyde with a molar ratio of formaldehyde to picoline in the range of 1:1 to 4:1, at a temperature ranging between 200° C. to 450° C., at a weight hourly space velocity in the range of 0.25 $hr^{-1}$–1.00 $hr^{-1}$ over a modified commercial zeolite catalyst to obtain the desired product.

In an embodiment of the present invention provides a process wherein, the vinylpyridine obtained is either 2-vinylpyridine or 4-vinylpyridine.

Still another embodiment, one of the reactant picoline is selected from 2-picoline and 4-picoline.

Still another embodiment, one of the catalyst is prepared by varying alkali and alkaline earth modified with a zeolite catalyst selected from a group consisting of ZSM-5, X, Y, mordenite and MCM-41.

In yet another embodiment, the catalyst used is preferably ZSM-5 pentasil type zeolite.

Yet another embodiment, the modification of the catalyst is carried out by alkali or alkaline earth metal ion selected from the group consisting of $Li^+$, $Na^+$, $K^+$, $Rb^+$, $Cs^+$, $Mg^{+2}$, $Ca^{+2}$, $Sr^{+2}$, $Ba^{+2}$ or two cation modified ZSM-5 like Cs—K-ZSM-5.

Still another embodiment the present invention provides a process, wherein the weight percent of the alkali or alkaline earth metal cation in ZSM-5 is varied from 1 weight percent to 4 weight percent.

Still another embodiment, the precursor to modify ZSM-5 catalyst by potassium ion or other elements is varied like K$^t$OBu, KOH, KF, KNO$_3$, K$_3$PO$_4$ and KOAc to improve the yield and selectivity of vinylpyridine.

Still another embodiment, the calcination temperature of modified zeolite is varied from 400° C. to 700° C.

Still another embodiment the reaction temperature of the catalytic zone in the process is varied from 200° C. to 450° C.

Still another embodiment the weight hourly space velocity (WHSV) is in the range of 0.25 to 1.0 hr$^{-1}$.

The following catalysts were used in the present process development HZSM-5 (SiO$_2$/Al$_2$O$_3$=30), NaY (SiO$_2$/Al$_2$O$_3$=5.0), H-Mordenite (SiO$_2$/Al$_2$O$_3$=12), and H-MCM-41 (SiO$_2$/Al$_2$O$_3$=31). Each zeolite was pelleted without binder, crushed and sized 18–30 mesh before the impregnation. The catalysts were modified by using required amount of alkali or alkaline earth cation nitrate by an impregnation method. In the case of potassium, different precursors like KO$^t$Bu, KF, KOAc, K$_3$PO$_4$ and KOH were used to modify ZSM-5 (30) catalyst. The required amount of precursor was taken in the form of nitrate or other soluble salts in 30 ml of distilled water. 4.0 g of the meshed catalyst was added to it and kept for soaking for 12 h. Then it was dried at 110° C. overnight and calcined at 420° C. for 4 h before using for the reaction. In a typical procedure for the synthesis of KO$^t$Bu modified ZSM-5 (30) catalyst is as follows, 7 g of HZSM-5 (30) was taken in 250 ml two-necked round bottom flask. Prior to the modification the catalyst was predried in oven at 100° C. for 1 h followed by flushing with nitrogen gas to remove the water present in the channels of the catalyst. In another round bottom flask required amount of KO$^t$Bu was dissolved in dry DMSO solvent. This solution was added to HZSM-5 (30) catalyst and kept stirring for 24 h in presence of nitrogen atmosphere. After 24 h stirring the resultant mixture was filtered, dried at 120° C. overnight and calcined at 400° C. for 4 h. The reactions were carried out in a fixed bed, continuous, down-flow pyrex reactor with 20 mm internal diameter at atmospheric pressure. All the catalysts were activated by calcination in a flow of air at 420° C. for 4 h and brought to the reaction temperature in situ. The catalyst temperature was measured with a thermocouple placed in the middle of the catalyst bed. A mixture of 2-picoline and formaldehyde were fed from a syringe pump at a rate of 2 ml.h$^{-1}$. The products from the reactor was cooled by circulating ice-cooled water and periodically collected. The quantitative analysis of product was carried out by gas chromatography (G.C.). The samples were analyzed by G.C. (Schimadzu-17A and 14B) fixed with an OV-17 (2 mm×⅛"OD) on chromosorb W-HP column and flame ionization detector. The retention times were compared with the authentic compounds. The products were confirmed by mass spectra, GC-mass and NMR techniques. The mass balance was >90–95%.

The following catalysts were used in the present process development HZSM-5 (SiO$_2$/Al$_2$O$_3$=30), NaY (SiO$_2$/Al$_2$O$_3$=5.0), H-Mordenite (SiO$_2$/Al$_2$O$_3$=12), and H-MCM-41 (SiO$_2$/Al$_2$O$_3$=31). Each zeolite was pelleted without binder, crushed and sized 18–30 mesh before the impregnation. The catalysts were modified by using required amount of alkali or alkaline earth cation nitrate by an impregnation method. In the case of potassium, different precursors like KO$^t$Bu, KF, KOAc, K$_3$PO$_4$ and KOH were used to modify ZSM-5 (30) catalyst. The required amount of precursor was taken in the form of nitrate or other soluble salts in 30 ml of distilled water. 4.0 g of the meshed catalyst was added to it and kept for soaking for 12 h. Then it was dried at 110° C. overnight and calcined at 420° C. for 4 h before using for the reaction. In a typical procedure for the synthesis of KO$^t$Bu modified ZSM-5 (30) catalyst is as follows, 7 g of HZSM-5 (30) was taken in 250-ml two-necked round bottom flask. Prior to the modification the catalyst was predried in oven at 100° C. for 1 h followed by flushing with nitrogen gas to remove the water present in the channels of the catalyst. In another round bottom flask required amount of KO$^t$Bu was dissolved in dry DMSO solvent. This solution was added to HZSM-5 (30) catalyst and kept stirring for 24 h in presence of nitrogen atmosphere. After 24 h stirring the resultant mixture was filtered, dried at 120° C. overnight and calcined at 400° C. for 4 h. The reactions were carried out in a fixed bed, continuous down-flow pyrex reactor with 20 mm internal diameter at atmospheric pressure. All the catalysts was activated by calcination in a flow of air at 420° C. for 4 h and brought to the reaction temperature in situ. The catalyst temperature was measured with a thermocouple placed in the middle of the catalyst bed. A mixture of 4-picoline and formaldehyde were fed from a syringe pump at a rate of 2 ml.h$^{-1}$.

The products from the reactor was cooled by circulating ice-cooled water and periodically collected. The quantitative analysis of product was carried out by gas chromatography (G.C.). The samples were analyzed by G.C. (Schimadzu-17A and 14B) fixed with an OV-17 (2 mm×⅛"OD) on chromosorb W-HP column and flame ionization detector. The retention times were compared with the authentic compounds. The products were confirmed by mass spectra, GC-mass and NMR techniques. The mass balance was >90–95%.

EXAMPLES

The present invention will be explained in more detail by the following examples, which do not limit the scope of the invention in any way.

Example-1

Synthesis of potassium modified ZSM-5.

Four grams of calcined HZSM-5 having SiO$_2$/Al$_2$O$_3$ molar ratio of 30 was taken in the form of 18–30 mesh size and soaked in 30 ml of the solution of potassium nitrate containing 0.4 g potassium (K) for 12 h. Then it was dried at 110° C. overnight and calcined at ~420° C. for 4 h before using for the reaction.

Example-2

Synthesis of cesium modified ZSM-5

The same procedure as given in Example-1 was used for the preparation of other metal ion ZSM-5 catalyst by using their inorganic salts as precursors. Cesium nitrate was used for Cs-ZSM-5.

Example-3

The modified ZSM-5 was used in the following reaction for the preparation of 2-vinylpyridine.

Cs-ZSM-5 (SiO$_2$/Al$_2$O$_3$=30) catalyst was packed in a pyrex reactor having an inner diameter of 20 mm with the length of 30–40 cms and the catalytic zone was heated at 300° C. Then a mixture of 2-picoline and formaldehyde in a molar ratio of 1:2 was fed from the top of the reactor at a weight hourly space velocity of 0.5 h$^{-1}$. The liquid product selectivity of 2-vinylpyridine was 92.8% at 40.4% conversion of 2-picoline at 4$^{th}$ hour on stream. The conversion of 2-picoline was in the range of 4–≧10% with 30–81.5% selectivity of 2-picoline at 300° C. over CsY, Cs-mordenite and Cs-MCM-41.

Example 4

The reaction of 2-picoline and formaldehyde was carried out over K-ZSM-5 (SiO$_2$/Al$_2$O$_3$=30) at 300° C. with 0.5 h$^{-1}$ weight hourly space velocity (W.H.S.V). The catalyst was 4 g with 18–30 mesh size and feed rate was 2 ml.hr$^{-1}$.

2-Picoline to formaldehyde was 1:2 molar. The liquid product selectivity of 2-vinylpyridine was 81.1% at 65.7% conversion of 2-picoline. 2-Ethylpyridine and other products were less than 18.9% selectivity. The reactor design and the other experimental details were as explained in Example-3 and the text.

Example-5

The reaction of 2-picoline and formaldehyde was carried out over Rb-ZSM-5 ($SiO_2/Al_2O_3=30$) at 300° C. with 0.5 $h^{-1}$ W.H.S.V. The experimental conditions are as explained in Example-3. The weight of the rubidium was 3 wt % in ZSM-5 catalyst. The percent liquid product selectivity of 2-vinylpyridine was 86.1% at 61.0% conversion of 2-picoline. The conversion of formaldehyde was ~100%.

Example-6

The reaction of 2-picoline and formaldehyde was carried out over Na-ZSM-5 ($SiO_2/Al_2O_3=30$) at 300° C. and 0.5 $h^{-1}$ W.H.S.V. The experimental conditions are as explained in Example-3. The weight of sodium was 3 wt % in ZSM-5 catalyst. The liquid product selectivity of 2-vinylpyridine was 99.7% at 35.0% conversion of 2-picoline during $4^{th}$ hour on stream.

Example-7

The reaction of 2-picoline and formaldehyde was carried out over CaZSM-5 ($SiO_2/Al_2O_3=30$) at 300° C. and 0.5 $h^{-1}$ W.H.S.V. The experimental conditions are as explained in Example-3. The weight of calcium was 3 wt % in ZSM-5 catalyst. The liquid product selectivity of 2-vinylpyridine was 72.2% at 57.2% conversion of 2-picoline during $4^{th}$ hour on stream. Mg-ZSM-5, Sr-ZSM-5 and Ba-ZSM-5 were also tested with lower yields.

Example-8

The ZSM-5 was modified using two cations like potassium (K) and cesium (Cs). The reaction of 2-picoline and formaldehyde was carried out over Cs—K-ZSM-5 (1 wt % Cs & 3 wt % K) at 300° C. and 0.5 $h^{-1}$ W.H.S.V. The experimental conditions were as given in Example-3. The liquid product selectivity of 2-vinylpyridine was 96.4% at 47.8% conversion of 2-picoline during $4^{th}$ hour on stream.

Example-9

The liquid product selectivities of 2-vinylpyridine were 96.2, 99.7, 99.8, 81.1, 98.9 and ≧99% at 82.4, 72.7, 54.3, 65.7, 56.8, and 61.8% conversions of 2-picoline when KO$^t$Bu, KOH, KF, $KNO_3$, $K_3PO_4$ and KOAc were used as precursors or as a potassium-source to prepare K-ZSM-5 (3 wt % K, $SiO_2/Al_2O_3=30$), respectively. The experimental conditions were as given in Example-3.

Example-10

The liquid product selectivities of 2-vinylpyridine were 93.3, 87.6, 81.1, and 80.7% at 49.1, 49.9, 65.7, and 66.4% conversions of 2-picoline over 1 wt % K-ZSM-5 ($SiO_2/Al_2O_3=30$), 2 wt % K-ZSM-5 (30), 3 wt % K-ZSM-5 (30) and 4 wt % K-ZSM-5 (30) catalysts, respectively. The experimental conditions were as given in Example-3. Similarly the weight percent of cesium (Cs) was varied and conversions and selectivities were studied. The activity for Cs-ZSM-5 was lower than that for K-ZSM-5 catalysts.

Example-11

The liquid product selectivities of 2-vinylpyridine were 88.1, 57.6, 92.8, 75.9 and 84.4% at 19.4, 28.3, 40.4, 61.5, and 37.8% conversions of 2-picoline at 200, 250, 300, 350, and 400° C. reaction temperatures over 3 wt % Cs-ZSM-5 ($SiO_2/Al_2O_3=30$) respectively. The other experimental conditions were as given in Example-3.

Example-12

The liquid product selectivities of 2-vinylpyridine were 73.6, 92.1, 74.6, and 74.0% at 60.3, 40.7, 63.9, and 62.7% conversions of 2-picoline with 1:1, 1:2, 1:3, and 1:4 molar ratio of 2-picoline/formaldehyde respectively. The catalyst was 3 wt % Cs-ZSM-5 ($SiO_2/Al_2O_3=30$). The other experimental conditions were as given in Example-3.

Example-13

The liquid product selectivities of 2-vinylpyridine were 90.5, 92.1, 73.0, and 75.5% at 40.9, 40.7, 54.9, and 57.1% conversions of 2-picoline at 0.25, 0.5, 0.75, and 1.0 $h^{-1}$ weight hourly space velocities (at $4^{th}$ hour on stream) respectively. The catalyst was 3 wt % Cs-ZSM-5 ($SiO_2/Al_2O_3=30$) and formaldehyde/2-picoline is 2 molar. The reaction temperature was 300° C. The other experimental conditions were as given in Example-3.

Example-14

With the experimental details as given in Example-3, the time on stream was studied and steady states activity and yields were obtained for ≧8 hours on stream.

Example-15

The modified ZSM-5 was used in the following reaction for the preparation of 4-vinylpyridine.

Cs-ZSM-5 ($SiO_2/Al_2O_3=30$) catalyst was packed in a pyrex reactor having an inner diameter of 20 mm with length 30–40 mm and the catalyst-packed part of the tube (catalytic zone) was heated to 300° C. Then a mixture of 4-picoline and formaldehyde in a molar ratio of 1:2 was fed from top of the reactor at a weight hourly space velocity of 0.5 hr.sup.-1. The liquid product selectivity of 4-vinylpyridine was 96.8% at 49.3% conversion of 4-picoline at $4^{th}$ hour on stream. The conversion of 4-picoline was in the range of 20–45% with 40–62% selectivity of 4-vinylpyridine at 300° C. over CsY, Cs-mordenite and Cs-MCM-41.

Example-16

The reaction of 4-picoline and formaldehyde was carried out over K-ZSM-5 ($SiO_2/Al_2O_3=30$) at 300° C. with 0.5 $h^{-1}$ weight hourly space velocity (W.H.S.V). The catalyst was 4 g with 18–30 mesh size and feed rate was 2 ml.$h^{-1}$. 4-picoline to formaldehyde was 1:2 molar. The liquid product selectivity of 4-vinylpyridine was 97.0% at 77.6% of the conversion of 4-picoline. 4-Ethylpyridine and other products were less than 3% selectivity. The reactor design and the other experimental details were as explained in Example-15 and the text.

Example-17

The reaction of 4-picoline and formaldehyde was carried out over Rb-ZSM-5 ($SiO_2/Al_2O_3=30$) at 300° C. with 0.5 $h^{-1}$ W.H.S.V. The experimental conditions are as explained in Example-15. The weight of the rubidium was 3 wt % in ZSM-5 catalyst. The percent liquid product selectivity of 4-vinylpyridine was 96.2% at 85.2% conversion of 4-picoline. The formaldehyde conversion was 100%.

Example-18

The reaction of 4-picoline and formaldehyde was carried out over Na-ZSM-5 ($SiO_2/Al_2O_3=30$) at 300° C. and 0.5 $h^{-1}$ W.H.S.V. The experimental conditions are as explained in Example-15. The weight of sodium (Na) was 3 wt % in ZSM-5 catalyst. The liquid product selectivity of 4-vinylpyridine was 99.3% at 76.9% conversion of 4-picoline during $4^{th}$ hour on stream.

Example-19

The reaction of 4-picoline and formaldehyde was carried out over Ca-ZSM-5 $SiO_2/Al_2O_3=30$) at 300° C. and 0.5 $h^{-1}$ W.H.S.V. The experimental conditions are as explained in Example-15. The weight of calcium was 3 wt % in ZSM-5 catalyst. The liquid product selectivity of 4-vinylpyridine was 83.9% at 37.2% conversion of 4-picoline during $4^{th}$ hour on stream. Mg-ZSM-5, Sr-ZSM-5 and Ba-ZSM-5 were also tested with lower yield.

Example-20

The ZSM-5 was modified using two cations like K and Cs. The reaction of 4-picoline and formaldehyde was carried out over Cs-K-ZSM-5 (1 wt %Cs & 3 wt % K) at 300° C. and 0.5 $h^{-1}$ W.H.S.V. The experimental conditions were as given in Example-15. The liquid product selectivity of 4-vinylpyridine was 96.1% at 69.8% conversion of 4-picoline during $4^{th}$ hour on stream.

Example-21

The liquid product selectivities of 4-vinylpyridine were 78.2, 99.3, 96.8, 97.3, and 95.3% at 80.2, 85.1, 91.9, 90.0, and 91.5% conversion of 4-picoline when KO$^t$Bu, KOH, KF, $K_3PO_4$ and KOAc were used as precursors or as a potassium- source to prepare K-ZSM-5 (3 wt % K, $SiO_2/Al_2O_3=30$), respectively. The experimental conditions were as given in Example-15.

Example-22

The liquid product selectivities of 4-vinylyridine were 87.8, 89.1, 97.0, and 68.7% at 63.3, 64.4, 77.6, and 76.6% conversion of 4-picoline over 1 wt % K-ZSM-5 ($SiO_2/Al_2O_3=30$), 2 wt %K-ZSM-5 (30), 3 wt %K-ZSM-5 (30) and 4 wt % K-ZSM-5 (30) catalysts respectively. The experimental conditions were as given in Example-15. Similarly the weight percent of cesium (Cs) was varied and conversion and selectivities were studied (determined). The activity for Cs-ZSM-5 was lower than that for K-ZSM-5 catalysts.

Example 23

The liquid product selectivities of 4-vinylpyridine were 73.4, 63.9, 96.8, 59.9, and 51.6% at 28.8, 57.4, 49.3, 66.2, and 65.3% conversion of 4-picoline at 200, 250, 300, 350 and 400° C. reaction temperature over 3 wt % Cs-ZSM-5 ($SiO_2/Al_2O_3=30$) respectively. The other experimental conditions were as given in Example-15.

Example 24

The liquid product selectivities of 4-vinylpyridine were 79.8, 96.8, 89.9, and 66.3% at 53.5, 49.3, 52.3, and 54.9% conversions of 4-picoline with 1:1, 1:2, 1:3, and 1:4 molar ratio of 4-picoline/formaldehyde respectively. The catalyst was 3 wt % Cs-ZSM-5 ($SiO_2/Al_2O_3=30$). The other experimental conditions were as given in Example-15.

Example 25

The liquid product selectivities of 4-vinylpyridine were 80.3, 96.8, 96.2, and 93.5% at 66.4, 49.3, 39.2, and 37.1% conversion of 4-picoline at 0.25, 0.5, 0.75 and 1.0 $h^{-1}$ weight hourly space velocities respectively. The catalyst was 3 wt % Cs-ZSM-5 ($SiO_2/Al_2O_3=30$) and formaldehyde/4picoline=2 molar. The reaction temperature was 300° C. The other experimental conditions were as given in Example-15.

Example 26

With the experimental details as given in Example-15, the time on stream was studied and steady state activity and yields were obtained for $\geq 8$ hours on stream.

What is claimed is:

1. An improved process for the preparation of vinylpyridine from corresponding picoline over modified zeolite catalyst in vapour phase which comprises reacting picoline with formaldehyde, at a temperature ranging between 200° C. to 450° C., at a weight hourly space velocity in the range of 0.25 $hr^{-1}$–1.00 $hr^{-1}$ over a modified zeolite catalyst, said catalyst is selected from the group consisting of ZSM-5, X, Y, mordenite and MCM-41, said catalyst is modified with one or more ions, said ions comprising one or more alkaline earth metal ions.

2. An improved process as claimed in claim 1, wherein the vinylpyridine obtained is either 2-vinylpyridine or 4-vinylpyridine.

3. An improved process as claimed in claim 1, wherein picoline used is selected from 2-picoline and 4-picoline.

4. An improved process as claimed in claim 1, wherein the weight percent of the ion in said catalyst used is in the range of 1 to 4 wt %.

5. An improved process as claimed in claim 1, wherein the precursor used to modify ZSM-5 catalyst by potassium ion or other elements, wherein potassium ions is selected from the group consisting of KOtBu, KOH, KF, KNO3, K3PO4 and KOAc to improve the yield and selectivity of vinylpyridine.

6. An improved process as claimed in claim 1, wherein the calcination temperature of modified zeolite used is varied between 400° C. to 700° C.

7. An improved process as claimed in claim 1, wherein the reaction temperature of the catalytic zone used is in the range of 300° C. to 400° C.

8. An improved process as claimed in claim 1, wherein a mole ratio of 2-picoline to formaldehyde is 1:2.

9. An improved process as claimed in claim 1, wherein a mole ratio of 2-picoline to formaldehyde is 1:1 to 4:1.

10. An improved process as claimed in claim 1, wherein the alkaline earth metal ions are selected from the group consisting of Mg, Ca, Sr and Ba.

11. An improved process as claimed in claim 1, wherein the modification of the catalyst is carried out between two or more modified ZSM-5.

12. An improved process as claimed in claim 1, said ions further comprising one or more alkali earth metal ions.

13. An improved process as claimed in claim 12, wherein the alkali earth metal ions are selected from the group consisting of Li, Na, K, Rb, and Cs.

* * * * *